United States Patent [19]

Kearney et al.

[11] 4,366,038
[45] Dec. 28, 1982

[54] METHOD OF CASTING IN PLACE AN ION-SENSITIVE MEMBRANE AND ION-SENSITIVE ELECTRODE USING SAID MEMBRANE

[75] Inventors: Susan D. Kearney, Weston; Gustav H. Dreier, Acton; Alan D. Cormier, Newburyport, all of Mass.

[73] Assignee: Instrumentation Laboratory Inc., Lexington, Mass.

[21] Appl. No.: 175,052

[22] Filed: Aug. 4, 1980

[51] Int. Cl.³ .......................... G01N 27/30; B29C 5/00
[52] U.S. Cl. .............................. 204/195 M; 264/267; 264/268
[58] Field of Search .................... 204/195 M, 1 A; 264/267, 268; 128/635

[56] References Cited

U.S. PATENT DOCUMENTS

| | | | |
|---|---|---|---|
| 3,562,129 | 2/1971 | Simon | 204/195 M |
| 3,562,130 | 2/1971 | Hoole et al. | 204/195 M |
| 3,706,649 | 12/1972 | Cosgrove et al. | 204/195 M |
| 3,753,887 | 8/1973 | Kedem et al. | 204/195 M |
| 3,767,553 | 10/1973 | Brown et al. | 204/195 M |
| 4,115,209 | 9/1978 | Freiser et al. | 204/1 T |
| 4,135,999 | 1/1979 | Schindler et al. | 204/195 M |
| 4,175,028 | 11/1979 | Payton | 204/296 |

FOREIGN PATENT DOCUMENTS 2025629 1/1980 United Kingdom .

OTHER PUBLICATIONS

Lavinia A. R. Pioda et al., Analytical Letters, 2(12), 665-674, (1969).
M. S. Frant et al., Science, vol. 167, pp. 987-988, 2/70.

*Primary Examiner*—G. L. Kaplan
*Attorney, Agent, or Firm*—Lowell H. McCarter

[57] ABSTRACT

A one-piece disposable electrode comprising a sealed chamber containing an electrolyte solution, silver-silver chloride conductor in the electrolyte solution in the chamber and a cast-in-place membrane essentially flush with an exterior wall of this chamber for exposure to a biological fluid whose ion content is to be measured.

28 Claims, 4 Drawing Figures

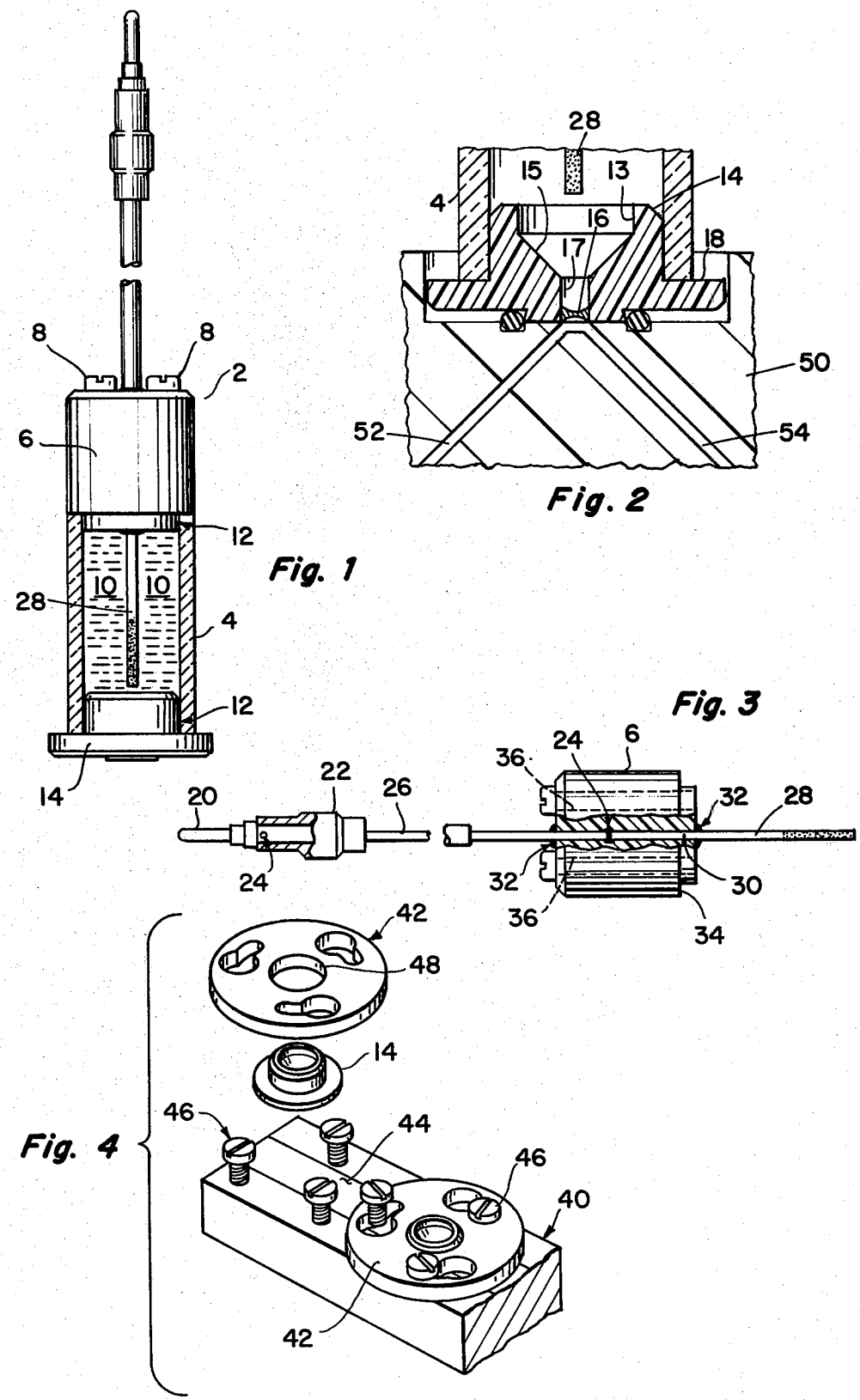

METHOD OF CASTING IN PLACE AN ION-SENSITIVE MEMBRANE AND ION-SENSITIVE ELECTRODE USING SAID MEMBRANE

BACKGROUND

This invention relates to an electrochemical electrode of the type used for ion activity measurements. Recently several ion sensitive electrodes containing certain macrocyclic compounds have been described in the literature and have become commercially available. A potassium ion responsive electrode employing, as its ion selective ionophore, a liquid organic sensing solution impregnated in a Millipore filter is described in an article by Pioda et al entitled "Highly Selective Potassium Ion Responsive Liquid-Membrane Electrode", Analytical Letters, vol. 2, pp. 665–674 (1969) and in U.S. Pat. No. 3,562,129. These publications describe the liquid organic sensing solutions as comprising either valinomycin, nonactin or monactin contained in diphenylether.

An article by Frant et al entitled "Potassium Ion Specific Electrode With High Selectivity for Potassium Over Sodium", Science, vol. 167, pp. 987–8 (1970) makes reference to a potassium ion measuring electrode having an ionophore comprising nonactin in Nujal-octanol, and to a commercially available electrode having a liquid organic ionophore comprising a mixture of valinomycin and an aromatic solvent. Examples of the solvents mentioned in the article are nitrobenzene and higher homologs, diphenylether, chlorobenzene, and bromobenzene.

Another commercially available potassium ion electrode employs a sensing solution containing a major portion of a non-aqueous hydrophobic solvent, such as decane and minor portions of valinomycin and the phospholipid, lecithin. Such sensing solution is supported between a pair of cellophane membranes in a sample measuring cell in which the sample contacts the outside surface of one of the membranes and KCl solution in which a silver chloride electrode is immersed contacts the outside of the other membrane.

As can be seen from the above summary of recent organic potassium ion measuring electrodes, liquid organic sensing solutions are employed which are either supported by a filter paper or a cellophane membrane. One purpose of our invention is to provide a potassium ion measuring electrode which employs an essentially solid ion sensitive barrier containing a macrocylic compound, which offers considerable ease of use over the liquid membrane electrodes, besides having excellent selectivity to the ion being measured.

More recently, U.S. Pat. No. 3,706,649 teaches a substantially solid ion sensitive barrier containing a macrocylic compound, mineral oil, and a lipid. This patent indicates that other solidification agents, i.e. collodian polystyrene, silica gel and colloidal silica when used in place of the lipid greatly diminished or eliminated the ion sensing properties of the solid ion sensitive barrier. In this arrangement it is necessary to put and hold in place a protective covering membrane having perforations therein over the ion sensitive barrier.

In U.K. patent application Ser. No. 2,025,629 A, published Jan. 23, 1980, there is disclosed an ion selective electrode assembly. A tube of plastic material defining a flow path through the electrode assembly contains in a portion of the tube wall an ion selective membrane bonded to the tube wall so that biological fluid slides past the membrane surface in a generally laminar flow.

In accordance with this invention, there is provided a disposable one-piece electrode system in which a half cell conductor is disposed in an electrolyte solution in a sealed chamber. A passage extends through one wall of the chamber to an external surface arranged for exposure at an angle to the flow of the sample solution to be analyzed. Disposed in that passage is a cast-in-place membrane with one surface essentially flush with the external surface of the chamber and an opposed surface that is in direct and intimate contact with the electrolyte solution. The half cell electrode may be placed closely adjacent the internal surface of the cast-in-place membrane such that the electrode system is compact, durable, reliable, maintainence free, virtually unbreakable and easily replaceable. The electrode system is placed in a fluid flow path so that the flow of the solution whose ion content is to be measured impinges directly on the cast-in-place membrane.

In a particular embodiment, the half-cell conductor is a silver-silver chloride wire; the electrolyte is sodium chloride-potassium chloride solution prepared as described herein and the cast-in-place membrane is about 1.5 millimeters in diameter; and an initial electrical resistance of about $10^8$ ohms and generally will not exceed $2 \times 10^9$ ohms during the life of the electrode. The electrode unit has an overall length of about 3.5 centimeters and a diameter of about 1.5 centimeters.

Other features and advantages will be seen as the following description of a particular embodiment progresses in conjunction with the drawings, in which:

FIG. 1 is a sectional view of the electrode in accordance with the invention;

FIG. 2 is an enlarged sectional view of the end cap portion of the electrode showing the cast-in-place membrane in relationship to a sample solution flow path;

FIG. 3 is a sectional view of the top cap of the electrode including a connector assembly;

FIG. 4 is illustrating the apparatus used in casting the cast-in-place membranes.

DESCRIPTION OF PARTICULAR EMBODIMENT

The reference electrode assembly 2 shown in FIG. 1 includes a top cap assembly 6, a barrel or hollow sleeve 4 and a membrane end cap 14 having a cast-in-place membrane. The top cap, sleeve, and end cap form a sealed chamber. In the preferred embodiment the sleeve 4 is a clear, rigid vinyl member having an outer diameter of about 12.5 millimeters, an inner diameter of about 10 millimeters, a length of about 22.5 millimeters. The top cap 6 preferably constructed of opaque polyvinyl chloride material has a length of about 14 millimeters and a diameter of about 12.5 millimeters. The top cap 6 is sealed to sleeve 4 such as by ultrasonic welding 12 or a solvent bond 12. Silver-silver chloride conductor 28 is soldered to the lead wire 26 (FIG. 3) at solder joint 24. The lead wire and conductor wire 28 extends through the central axial extending passage 30 in top cap 6 and is connected to connector assembly 20. The cast-in-place membrane end cap 14, preferably also of opaque polyvinyl chloride, has a flange 18 (FIG. 2) of about 17.5 millimeters in diameter and about 6 millimeters in thickness has a generally cylindrical body portion which is received within and sealed to the end of sleeve 4 (FIG. 1) opposite top cap 6 with either an ultrasonically welded bond 12 or solvent bond 12. In the body portion of the membrane end cap 14 is a well formed by a cylindrical opening 13 merging into a generally frusto-conical shape 15 having an upper diameter of about 6.5 millimeters and a lower diameter ranging from about 1.5 to about 2.0 millimeters in diameter. The lower portion of the frusto-conical opening extends into a passageway 17 through the end cap. In the preferred embodiment the frusto-conical opening terminates in a cylindrical passageway 17 as illustrated in FIG. 2. The passageway 17 has a length of about two millimeters. Secured in passageway 17 adjacent the external surface of the end cap is a cast-in-place membrane 16. The membrane solution from which the membrane is cast, comprises a solution of an inert plastic matrix material, a plasticizer, a solvent and an ionophore active ingredient. The tip of the silver-silver chloride conductor extends into the sealed chamber and is spaced from the membrane 16.

It has been found that the frusto-conical shape of the opening in the membrane end cap is important in assuring accurateness of the electrode. Most of the electrodes have straight sides in the sealed chamber. We have observed, in straight sided chambers, that if any gas bubbles are entrapped they have a tendency to remain in the electrolyte in the vicinity of the membrane and therefore may effect the electrode performance. Using the frusto-conical shape in the end cap in which the cast-in-place membrane is positioned allows any entrapped gas to be relatively easily dispersed since any entrapped gas in the vicinity of the membrane will follow the contour of the frusto-conical surface and be dispersed to the upper portion of the sealed chamber where it does not appear to effect electrode performance. The frusto-conical surface also allows the area of the membrane to be substantially less than prior art ion selective membranes.

The electrolyte or electrode fill solution 10 in the preferred embodiment is prepared by dissolving sodium chloride, potassium chloride, triethanolamine and formaldehyde in distilled deionized water. The pH of the solution is then adjusted by adding dilute sulfuric acid to the electrolyte until the pH is about 7.4±0.1. The resulting electrolyte will have a preferred molar concentration of approximately 140 millimole per liter sodium chloride, 5 millimole per liter potassium chloride, 3 millimole per liter triethanolamine, and 54 millimole per liter formaldehyde.

In a preferred embodiment for preparing a cast-in-place potassium selective electrode a casting solution will consist of technical grade polyvinyl chloride as the matrix material, dioctyl sebacate as the plasticizer, tetrahydrofuran as the solvent and valinomycin as the active ingredient. The membrane solution is prepared by adding to a vial the dioctyl sebacate plasticizer, the valinomycin and polyvinyl chloride particles, followed by the addition of the tetrahydrofuran solvent. The vial is capped with a rubber stopper and mixed until all the solids have dissolved. The container is stored until needed. Before use the casting solution is deaerated. The solution is placed in a bell jar or vacuum cabinet and subjected to a vacuum of 20 to 25 inches mercury. The solution may bubble as dissolved air escapes. The vacuum should be held at this level for ten minutes before bringing the solution back to atmospheric pressure. The solution is then ready for immediate use.

The casting procedure requires that the end cap 14 and Teflon surface 44 of the casting fixture 40 (FIG. 4) be cleaned of any lint or plastic dust. The end cap 14 is placed over the Teflon surface 44 with the frusto-conical 15 opening up. The clamp 42 is then placed over each end cap 14 on the casting fixture 40 and secured snuggly with fastening means 46 taking care to keep the cap level. Approximately 7 to 20 microliters of the membrane solution is placed in passageway 17 through the frusto-conical opening in the end using a 20 microliter disposable pipette. If air is entrapped in the membrane solution in the end cap the tip of the pipette may be used to remove it. The cast-in-place membranes in the end caps are allowed to dry for about one hour under a dust cover permitting enough air circulation to allow good drying. The end cap 14 is removed from the casting fixture 40 after the drying period and is inspected with a hand lens for defects. Satisfactory membranes are those that do not contain excessive lint, bubbles, holes or particles, double membranes or a recessed membrane. The preferred configuration of the membrane is shown in FIG. 2 at 16. The membrane 16 should be adjacent to the lower portion of the opening 17 and may have top and bottom concave surfaces.

The sealed chamber defined by the inner wall of electrode sleeve 4 and top cap 6 and end cap 14 is filled with electrolyte 10 through opening 36 (shown in FIG. 3). The other passage 36 is to allow air to escape from the chamber during the filling process. After approximately 1.5 milliliter of the electrolyte solution is placed in the chamber the passageways 36 are sealed by non-conducting sealing means 8, preferably threaded nylon screws or bolts.

The external portion of the end cap 14 is secured in a cuvette 50 (partially shown in FIG. 2) having sample entrance and exit passageways 52, 54 such that the sample whose ion content is to be measured impinges directly on the ion selective cast-in-place membrane. The exposed area of the external surface of the membrane 16 is about two square millimeters.

This ion-selective electrode is a compact and inexpensive unit which is virtually unbreakable and easily replaceable. Electrolyte 10 is sealed within the electrode chamber and does not require replacement or replenishment over the useful life of the electrode which is typically in excess of one month.

While a particular embodiment of the invention has been shown and described, various modifications will be apparent to those skilled in the art and therefore it is not intended that the invention be limited to the disclosed embodiment or details thereof, and departures may be made therefrom within the spirit and scope of the invention.

What is claimed is:

1. Electrochemical electrode apparatus for use in determination of potassium ion activity in a solution consisting of an electrically insulating material defining a chamber; a passage through a wall of said chamber to an external surface arranged for exposure to a sample solution to be measured; a cast-in-place potassium sensitive membrane secured in said passage, said membrane having an external surface essentially flush with said external surface of said chamber and an internal surface in said chamber, the exposed area of said internal surface of said membrane being substantially the same as the exposed area of said external surface of said membrane, said membrane cast from a solution containing plastic matrix material, a plasticizer, a solvent and an ion sensitive active ingredient to form a substantially solid potassium ion sensitive barrier; an electrolyte solution of sodium chloride, potassium chloride, triethanolamine and formaldehyde in deionized water in said chamber in contact with said internal surface of said cast-in-place membrane, and half-cell conductor disposed in said electrolyte solution in said chamber for producing an electric potential.

2. The apparatus of claim 1 wherein said half-cell conductor is a silver-silver halide conductor.

3. The apparatus of claim 1 wherein said electrolyte solution is adjusted to a pH value of from about 7.3 to about 7.5.

4. The apparatus of claim 1 wherein said external surface of said cast-in-place membrane is less than about five square millimeters.

5. The apparatus of claim 1 including a well of frusto-conical shape forming a portion of the passage such that the cast-in-place membrane is positioned in the smaller cross-sectional area portion of the passage.

6. The apparatus of claim 1 including means to secure said apparatus in a sample fluid flow path such that the sample fluid whose potassium ion content is to be measured impinges directly on the cast-in-place membrane.

7. Electrochemical potassium ion sensitive electrode apparatus for use in determination of ion activity in solution consisting of an electrically insulating material defining a chamber; a sodium chloride-potassium chloride electrolyte solution in said chamber; a silver-silver chloride half-cell conductor disposed in said electrolyte solution in said chamber for producing an electrical potential; a passage through a wall of said chamber to an external surface arranged for exposure to a flowing sample; a cast-in-place membrane secured in said passage, said membrane having an external surface essentially flush with said external surface of said chamber defining structure and an internal surface in said chamber in direct and intimate contact with said electrolyte solution, the exposed area of said external membrane surface being about two square millimeters, and the electrical resistance of the junction between said silver-silver chloride conductor and the sample solution to be measured being less than about $2 \times 10^9$ ohms.

8. The apparatus of claim 7 including a well of frusto-conical shape forming a portion of the passage such that the cast-in-place membrane is positioned in the smaller cross sectional area portion of the passage.

9. The apparatus of claim 7 including means to secure the electrode in a sample fluid flow path such that the sample fluid impinges directly on the cast-in-place membrane.

10. An electrode for measuring the activity of potassium ions in an aqueous solution consisting of
 (a) a hollow tube open at both ends,
 (b) a top cap closing one end of said tube,
 (c) an end cap disposed in covering relationship across the other end of said tube, said end cap having a frusto-conical opening, said opening containing a cast membrane therein, said cast membrane being cast directly in place in said frusto-conical opening in said end cap,
 (d) an internal reference electrode positioned in said tube extending through said top cap and spaced from said end cap, and
 (e) an electrolyte solution in said tube for making electrical contact between said membrane and said internal reference electrode.

11. The electrode of claim 10 wherein the membrane is positioned adjacent a small diameter end of said frusto-conical opening.

12. The electrode of claim 11 including a means to secure said electrode in a sample fluid flow path such that the sample fluid whose potassium ion content is to be measured impinges directly on the cast membrane.

13. A disposable electrode for use in determination of the activity of an ionic species in solution consisting of:
 (a) a reference solution,
 (b) a container having a top cap and an end cap confining said reference solution, said end cap having passageway for communication between interior and exterior of said container, the passageway in the form of a well of frusto-conical shape such that the smaller diameter opening is exposed to exterior of said container, said top cap having two radially opposed passageways sealed at their exteriors,
 (c) an integral electrode element in contact with said reference solution and extending through a central passageway in said top cap for contact with an external measuring device, and
 (d) an ion selective cast-in-place membrane disposed in a covering relationship across the small diameter opening in said end cap, said membrane cast from a membrane solution containing plastic matrix material, a plasticizer, a solvent and an ion sensitive active ingredient.

14. A disposable electrode assembly sensitive to potassium ions in solution, consisting of, in combination,
 (a) a hollow container of electrically insulating material and having at least one opening therein,
 (b) a cast-in-place membrane of electrically insulating material disposed in covering relationship across said opening,
 (c) an electrolyte solution in said hollow container, and
 (d) a reference electrode positioned in said container in electrical contact with said electrolyte solution said opening having a frusto-conical shape with the larger diameter opening facing the interior of said container and said membrane positioned in the smaller diameter of this frusto-conical shape.

15. An electrode for use in determination of ion activity in an aqueous solution consisting of:
 an electrically conductive inner element disposed in an electrically insulating sleeve, said sleeve having a top cap covering one opening in said sleeve, said top cap having at least two openings therethrough, one of said openings providing a passageway for said inner element to the exterior, and an end cap fixed to second opening in said sleeve, said end cap having an attached cast-in-place membrane covering a frusto-conical opening in said end cap, and a reference solution positioned in a sealed chamber provided by the sleeve, the top cap and the end cap.

16. A disposable system for substantially instantaneously measuring the activity of selected ions in solutions having both the selected and other ions consisting of:
 (a) a container including a reference solution therein,
 (b) a top cap on said container having at least two openings extending therethrough for communication with the exterior of said container,
 (c) an end cap on said container, said end cap having a frusto-conical shaped passageway terminating in a cylindrical passageway extending from the interior of said container to the exterior thereof, said cylindrical passageway having a cast-in-place membrane adjacent the exterior surface of said end cap, (d) a reference electrode positioned in said container and communicating with the exterior through one of said openings in said top cap and bonded in said opening, said second opening in said top cap providing a filling port for placing the reference solution in said container, and (e) a sealing means in said second opening.

17. An end cap for a disposable electrode consisting of an electrically insulating material of generally circular diameter, said end cap having a frusto-conical opening therethrough and a cast-in-place membrane in the smaller diameter opening in said frusto-conical opening.

18. The end cap of claim 17 wherein the surfaces of said cast-in-place membrane are concave.

19. The end cap of claim 17 wherein the cross-sectional area of said cast-in-place membrane does not exceed about 5 square millimeters.

20. The end cap of claim 17 wherein said membrane is cast from a solution comprising polyvinyl chloride, dioctyl sebacate, tetrahydrofuran and valinomycin.

21. The end cap of claim 17 wherein said end cap is opaque polyvinyl chloride.

22. The end cap of claim 17 wherein said frusto-conical opening terminates in a cylindrical passageway.

23. A method for forming an end cap for a disposable ion sensitive electrode consisting of placing an end cap having a frusto-conical opening therethrough in a casting clamp such that the small diameter of the frusto-conical opening is positioned adjacent a casting fixture leaving the larger diameter opening of said frusto-conical opening exposed, placing in said exposed frusto-conical opening an amount of a membrane casting solution not to exceed about 20 microliters and allowing the solvent in the membrane casting solution to evaporate leaving a bonded cast membrane in the smaller diameter of said frusto-conical opening.

24. The method of claim 23 wherein said membrane casting solution comprising polyvinyl chloride, dioctyl sebacate, tetrahydrofuran and valinomycin.

25. The method of claim 23 wherein the cross-sectional area of the membrane does not exceed about 5 square millimeters.

26. The method of claim 23 wherein said membrane casting solution is deaerated prior to casting.

27. The method of claim 26 wherein said casting solution is placed in a cylindrical passageway terminating said frusto-conical opening.

28. A method of forming a membrane chemically bonded to an electrode end cap, the method consisting of:

(a) dissolving an organic plastic matrix material, plasticizer and a solvent soluble ionophore material in a solvent to form a membrane solution, (b) placing the resulting membrane solution in a frusto-conical opening in a solvent soluble end cap for a disposable electrode end cap.

* * * * *